US00PP32686P2

(12) United States Plant Patent
Legutko

(10) Patent No.: US PP32,686 P2
(45) Date of Patent: Dec. 22, 2020

(54) ***BEGONIA* PLANT NAMED 'LEGDBLRED'**

(50) Latin Name: *Begonia semperflorens*
Varietal Denomination: Legdblred

(71) Applicant: Wieslaw Legutko, Jutrosin (PL)

(72) Inventor: Wieslaw Legutko, Jutrosin (PL)

( * ) Notice: Subject to any disclaimer, the term of this patent is extended or adjusted under 35 U.S.C. 154(b) by 0 days.

(21) Appl. No.: 16/873,400

(22) Filed: Apr. 4, 2020

(51) Int. Cl.
*A01H 5/02* (2018.01)
*A01H 6/18* (2018.01)

(52) U.S. Cl.
USPC ..... Plt./349
CPC ..... *A01H 6/185* (2018.05)

(58) Field of Classification Search
USPC ..... Plt./349
CPC ..... A01H 6/185; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Begonia* plant named 'Legdblred', characterized by its broadly upright plant habit; roughly globular in plant form; moderately vigorous growth habit; freely basal branching habit; reddish green-colored leaves; freely flowering habit; long flowering period; relatively small, self-cleaning double-type and occasional single-type flowers that are deep red in color; and good garden performance.

2 Drawing Sheets

Figure 1:
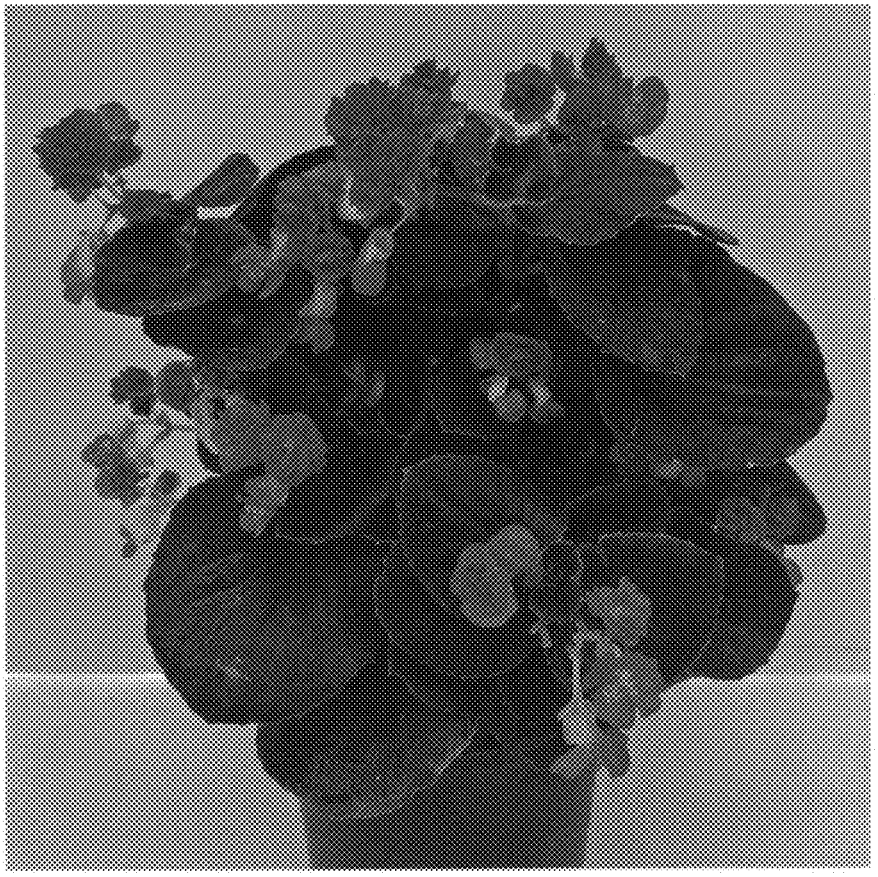

Botanical designation: *Begonia semperflorens.*
Cultivar denomination: 'LEGDBLRED'.

BACKGROUND OF THE INVENTION

The present invention relates to a new and distinct cultivar of *Begonia* plant, botanically known as *Begonia semperflorens* and hereinafter referred to by the name 'Legdblred'.

The new *Begonia* plant is a product of a planned breeding program conducted by the Inventor in Jutrosin, Poland. The objective of the breeding program is to create new *Begonia* plants with uniform plant habit, numerous attractive double flowers and good garden performance.

The new *Begonia* plant originated from a cross-pollination made by the Inventor on Aug. 12, 2019 in Jutrosin, Poland of a proprietary seedling selection of *Begonia semperflorens* identified as code number 4519/1s, not patented, as the female, or seed, parent with *Begonia semperflorens* 'Indira Rose', not patented, as the male, or pollen, parent. The new *Begonia* plant was discovered and selected by the Inventor as a single flowering plant within the progeny of the stated cross-pollination in a controlled greenhouse environment in Jutrosin, Poland on Aug. 30, 2010.

Asexual reproduction of the new *Begonia* plant by terminal vegetative cuttings taken in a controlled greenhouse environment in Jutrosin, Poland since September, 2010 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Legdblred'. These characteristics in combination distinguish 'Legdblred' as a new and distinct *Begonia* plant:

1. Broadly upright plant habit; roughly globular in plant form.
2. Moderately vigorous growth habit.
3. Freely basal branching habit.
4. Reddish green-colored leaves.
5. Freely flowering habit; long flowering period.
6. Relatively small, self-cleaning double-type and occasional single-type flowers that are deep red in color.
7. Good garden performance.

Plants of the new *Begonia* differ primarily from plants of the female parent selection in the following characteristics:

1. Leaves of plants of the new *Begonia* are reddish green in color whereas leaves of plants of the female parent selection are green in color.
2. Plants of the new *Begonia* produce mostly double flowers whereas plants of the female parent selection produce semi-double flowers.
3. Flowers of plants of the new *Begonia* are darker red in color than flowers of plants of the female parent selection.

Plants of the new *Begonia* differ primarily from plants of the male parent, 'Indira Rose', in flower color as flowers of plants of the new *Begonia* are deep red in color whereas flowers of plants of 'Indira Rose' are pink in color.

Plants of the new *Begonia* can be compared to plants of *Begonia semperflorens* 'Gumdrop Red', not patented. In side-by-side comparisons, plants of the new *Begonia* differed primarily from plants of 'Gumdrop Red' in the following characteristics:

1. Plants of the new *Begonia* are more vigorous than plants of 'Gumdrop Red'.
2. Leaves of plants of the new *Begonia* are reddish green in color whereas leaves of plants of 'Gumdrop Red' are green in color.

Plants of the new *Begonia* can also be compared to plants of *Begonia* X *hybrida* 'Baby Wing Red', not patented. In side-by-side comparisons, plants of the new *Begonia* differed primarily from plants of 'Baby Wing Red' in the following characteristics:

1. Plants of the new *Begonia* are more compact and shorter than plants of 'Baby Wing Red'.
2. Leaves of plants of the new *Begonia* are reddish green in color whereas leaves of plants of 'Baby Wing Red' are green in color.
3. Plants of the new *Begonia* produce mostly double flowers whereas plants of the 'Baby Wing Red' produce single flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1 of 2) comprises a side perspective view of a typical plant of 'Legdblred' grown in a container.

Figure 2:
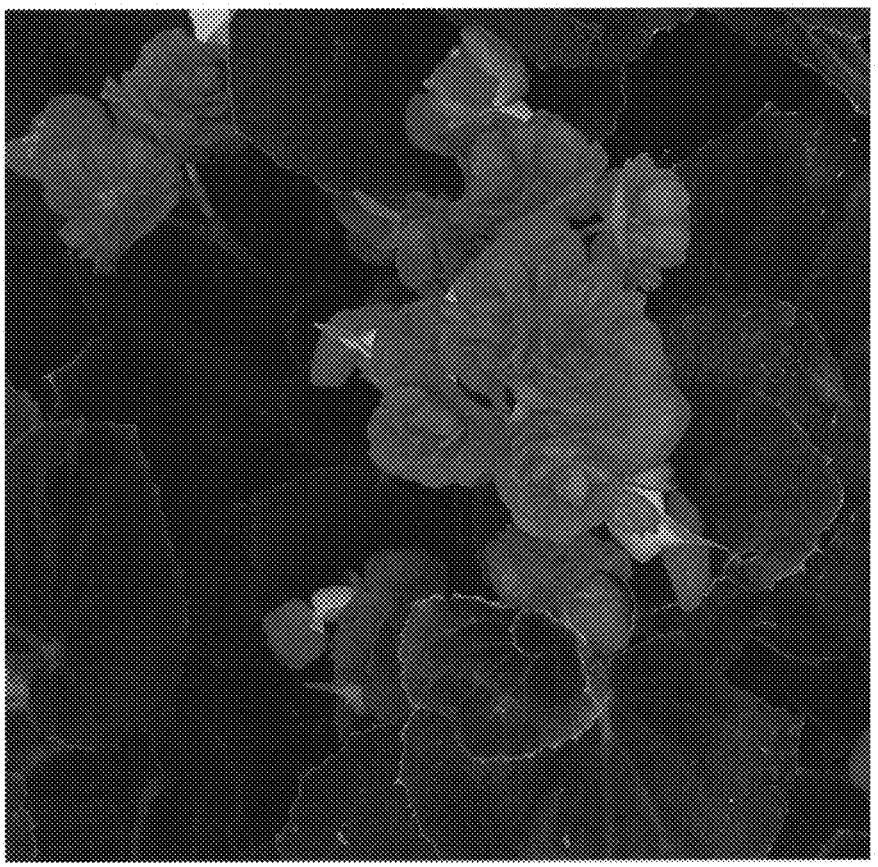

The photograph on the second sheet (FIG. 2 of 2) is a close up view of typical leaves and flowers of 'Legdblred'.

DETAILED BOTANICAL DESCRIPTION

The aforementioned photographs and following observations and measurements describe plants grown during the autumn and winter in 10.8-cm containers in a glass-covered greenhouse in Loudon, N.H. and under cultural practices typical of commercial *Begonia* production. During the production of the plants, average daily temperatures ranged from 19° C. to 21° C. Plants were grown under long day/short night conditions and were pinched three weeks after planting. Plants were 14 weeks from planting when the photographs and description were taken. In the following description, color references are made to The Royal Horticultural Society Colour Chart, 2015 Edition, except were general terms of ordinary dictionary significance are used. Measurements were taken on individual plants.

Botanical classification: *Begonia semperflorens* 'LEGDBL-RED'.

Parentage:

*Female, or seed, parent.*—Proprietary selection of *Begonia semperflorens* identified as code number 4519/1s, not patented.

*Male, or pollen, parent.*—*Begonia semperflorens* 'Indira Rose', not patented.

Propagation:

*Type.*—By terminal vegetative cuttings.

*Time to initiate roots, summer.*—About five to seven days at temperatures ranging from 24° C. to 27° C.

*Time to initiate roots, winter.*—About seven to nine days at temperatures ranging from 21° C. to 24° C.

*Time to produce a rooted young plant, summer.*—About four weeks at temperatures ranging from 21° C. to 24° C.

*Time to produce a rooted young plant, winter.*—About five weeks at temperatures ranging from 16° C. to 21° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching; medium density; plants of the new *Begonia* have not been observed to form tubers to date.

Plant description:

*Plant habit and form.*—Broadly upright plant habit; roughly globular in plant form.

*Growth habit.*—Moderately vigorous growth habit and moderate growth rate.

*Branching habit.*—Freely basal branching habit; multiple basal shoots and lateral branches potentially developing at every node; dense and bushy plant habit.

*Plant height.*—About 15.5 cm.

*Plant width.*—About 20 cm.

*Basal branches.*—Length: About 9 cm to 12 cm. Diameter: About 4 mm to 5 mm. Internode length: About 2 cm to 2.2 cm. Aspect: Erect to about 30° from vertical. Strength: Strong, flexible. Texture and luster: Smooth, glabrous; glossy. Color, developing and developed: Close to 144A.

*Leaves.*—Arrangement: Alternate; simple. Length: About 5.5 cm to 6.5 cm. Width: About 5.5 cm to 6 cm. Shape: Roughly spatulate to orbicular with cordate tendencies; leaves becoming more cordate in shape with development. Apex: Obtuse. Base: Truncate to obtuse. Margin: Irregularly serrate; not undulate. Texture and luster, upper surface: Smooth, glabrous; glossy. Texture and luster, lower surface: Smooth, glabrous; moderately glossy. Venation pattern: Palmate. Color: Developing leaves, upper and lower surfaces: Close to 144A variably overlain with close to 187A. Fully expanded leaves, upper surface: Close to 144A variably overlain with close to 187A; venation, close to 144A. Fully expanded leaves, lower surface: Close to 144A; venation, close to 144A. Petioles: Length: About 2.5 cm to 3.5 cm. Diameter: About 4 mm by 6 mm. Texture and luster, upper and lower surfaces: Smooth, glabrous; glossy. Strength: Strong, flexible. Color, upper and lower surfaces: Close to 144A. Stipules: Quantity and appearance: Two leafy stipules positioned at base of the leaf petiole. Length: About 1 cm. Width: About 5 mm to 7 mm. Shape: Deltoid. Apex: Acute. Base: Truncate. Margins: Finely serrate. Texture and luster, upper and lower surfaces: Smooth, glabrous; moderately glossy. Color, upper and lower surfaces: Close to 144A.

Flower description:

*Flower form and flowering habit.*—Relatively small flowers arranged in dichasial cymes with typically five to seven flowers per inflorescence; flowers face upright to outwardly and positioned above and beyond the foliar plane; flowers mostly sterile double-types, occasionally male single-types develop; freely flowering habit with numerous cymes developing per plant.

*Natural flowering season.*—Under natural season conditions, plants flower continuously from early June to October in Poland.

*Flower longevity*.—Individual flowers last about ten days on the plant; flowers not persistent.

*Fragrance*.—None detected.

*Inflorescence height*.—About 4 cm to 5 cm.

*Inflorescence diameter*.—About 4 cm to 5 cm.

*Flower buds*.—Length: About 5 mm. Diameter: About 7 mm. Shape: Lenticular, flattened. Texture and luster: Smooth, glabrous; slightly glossy. Color: Close to 62A.

*Single-type male flowers*.—Diameter: About 1.4 cm to 1.6 cm. Depth: About 1.5 cm to 1.7 cm. Shape: Rotate. Tepals: Quantity and arrangement: About five to seven arranged in a single whorl; tepaloids not observed. Length: About 7.5 mm. Width: About 7.5 mm. Shape: Spatulate. Apex: Obtuse. Base: Obtuse to truncate. Margin: Entire, not undulate. Texture and luster, upper and lower surfaces: Smooth, glabrous; somewhat velvety; slightly glossy. Color: When opening, upper and lower surfaces: Close to 53A. Fully opened, upper and lower surfaces: Close to 53A, towards the base, close to NN155D; venation, similar to lamina; color becoming closer to darker than 52A.

*Double-type sterile flowers*.—Diameter: About 1.8 cm to 2.2 cm. Depth: About 1.4 cm to 1.8 cm. Shape: Spherical. Tepals and tepaloids: Quantity and arrangement: About 50 to 70 tepals and tepaloids arranged in numerous whorls. Length, outer whorl: About 1 cm. Width, outer whorl: About 7.5 mm. Shape: Narrowly oblanceolate to narrowly spatulate. Apex: Emarginate. Base: Cuneate. Margin: Entire, not undulate. Texture and luster, upper and lower surfaces: Smooth, glabrous; slightly glossy. Color: When opening, upper and lower surfaces: Close to 53A. Fully opened, upper and lower surfaces: Close to 53A, towards the base, close to NN155D; venation, similar to lamina; color becoming closer to darker than 52A.

*Flower bracts*.—Quantity and arrangement: Two positioned at the top of the peduncle. Length: About 6 mm to 8 mm. Width: About 1 cm to 1.2 cm. Shape: Roughly lenticular. Apex: Obtuse. Base: Cordate. Margin: Entire. Texture and luster, upper and lower surfaces: Smooth, glabrous; moderately glossy. Color, upper and lower surfaces: Close to 53A.

*Peduncles*.—Length: About 2.5 cm to 3.5 cm. Diameter: About 2 mm. Angle: About 30° from lateral branch axis. Strength: Strong, flexible. Texture and luster: Smooth, glabrous; glossy. Color: Close to 144A to 144B.

*Pedicels*.—Length: About 1 cm to 1.5 cm. Diameter: About 1.5 mm. Angle: About 30° to 45° from peduncle axis. Strength: Strong, flexible. Texture and luster: Smooth, glabrous; glossy. Color: Close to 62A to 62B.

*Reproductive organs, present on single-type male flowers*.—Stamens: Stamen development has only been observed on single-type male flowers and not on double-type sterile flowers. Quantity: Typically three, bi-parted. Filament length: About 7 mm. Filament color: Close to 62A. Anther size: About 0.75 mm by 1.5 mm. Anther shape: Oblong. Anther color: Close to 12A. Pollen amount: None observed. Pistils: Pistil development has not been observed on single-type male and double-type sterile flowers.

*Seeds and fruits*.—To date, seed and fruit development have not been observed on plants of the new *Begonia*.

Pathogen & pest resistance: To date, resistance to pathogens and pests common to *Begonia* plants has not been observed on plants of the new *Begonia*.

Garden performance: To date, plants of the new *Begonia* have been observed to have good garden performance.

It is claimed:

1. A new and distinct *Begonia* plant named 'Legdblred' as illustrated and described.

* * * * *